United States Patent
Pabst et al.

(10) Patent No.: US 6,384,277 B1
(45) Date of Patent: May 7, 2002

(54) METHOD OF PRODUCING N-ALKYL-N'-NITROGUANIDINE

(75) Inventors: Winfried Pabst; Rainer Schirra, both of Lohmar (DE)

(73) Assignee: Dynamit Nobel GmbH Explosivstoff-und Systemtechnik, Troisdorf (DE)

( * ) Notice: Subject to any disclaimer, the term of this patent is extended or adjusted under 35 U.S.C. 154(b) by 0 days.

(21) Appl. No.: 09/856,714

(22) PCT Filed: Nov. 25, 1999

(86) PCT No.: PCT/EP99/09142

§ 371 Date: Sep. 7, 2001

§ 102(e) Date: Sep. 7, 2001

(87) PCT Pub. No.: WO00/31025

PCT Pub. Date: Jun. 2, 2000

(30) Foreign Application Priority Data

Nov. 25, 1998 (DE) .......................................... 198 54 511
Sep. 29, 1999 (DE) .......................................... 199 46 321

(51) Int. Cl.⁷ ............................................. C07C 279/36
(52) U.S. Cl. ..................................................... 564/108
(58) Field of Search ........................................ 564/108

(56) References Cited

U.S. PATENT DOCUMENTS 5,783,734 A * 7/1998 Gallenkamp

OTHER PUBLICATIONS

Eistert, Liebigs Ann. Chem., vol. 750, pp. 1–11 (1971).*
McKay, J. Am. Chem. Soc., vol. 69, pp. 3028–3030 (1947).*

* cited by examiner

Primary Examiner—Michael L. Shippen
(74) Attorney, Agent, or Firm—Antonelli, Terry, Stout & Kraus, LLP

(57) ABSTRACT

The invention relates to a method of producing N-alkyl-N'-nitroguanidine. According to said method, an alkyl amine solution is added to a nitroguanidine or nitroguanidine nitrate suspension at temperatures of >60° C. and the ammonia formed is removed.

14 Claims, No Drawings

METHOD OF PRODUCING N-ALKYL-N'-NITROGUANIDINE

The invention relates to a new method for the preparation of N-alkyl-N'-nitroguanidine.

A method for the preparation of N-methyl-N'-nitroguanidine, in which S-methylisothiuronium sulphate is nitrated in the usual manner and in which, subsequently in a second reaction stage, the methyl mercapto-group is substituted by methylamine, is described in JACS 76,1877 (1954). The disadvantage of this is that it is a two-stage conversion. Whilst the yields in the two stages are very good, the splitting-off of methylmercaptan, above all when carried out on a commercial scale, raises problems in terms of process engineering.

It is known, furthermore, that N-methyl-N'-nitroguanidine can be obtained by reacting an alkaline solution (potassium hydroxide) of nitroguanidine with methylamine hydrochloride at 60° C. (JACS 69,3028 (1947)). In order to remove inorganic impurities, in the case of this method it is necessary to provide up to two recrystallizations. As a result, yield losses cannot be avoided.

A method for the preparation of N-methyl-N'-nitroguanidine, in which nitroguanidine is reacted with aqueous methylamine solution at temperatures between 0° C. and 40° C., is described in DE-A-19 61 16 54. What is disadvantageous about this method is the fact that long reaction times of 24 hours result on account of the low reaction temperatures.

An object of the present invention has been to provide a method that enables good yields of N-alkyl-N'-nitroguanidine to be produced under conditions that are as selective as possible and with clearly reduced reaction times. Surprisingly, it has been possible to achieve this object by means of a method that has the features of the main claim. Preferred embodiments are characterised by the subclaims.

In accordance with the invention metered doses of an alkylamine solution are added to a suspension of nitroguanidine at temperatures >60° C., preferably at temperatures of 60 to 90° C., in particular preferably at temperatures of 60 to 75° C. In this connection, by alkylamine is to be understood, a branched or non-branched low alkylamine with 1 to 6 C-atoms, benzylamine or cyclohexylamine, preferably a hexyl-, pentyl-, tert.-butyl, butyl-, isopropyl-, propyl-, ethyl or methylamine, in particular preferably methylamine. Metered additions of a 40% methylamine solution are preferably added. In this connection, the equilibrium is shifted in the direction of the reaction end product by removing, preferably expelling, the ammonia that is formed. Advantageously, this happens in accordance with the invention by passing through air, nitrogen, $CO_2$ or other suitable gases. The ammonia that is formed can also be captured by adding acid, for example nitric acid, or dry ice ($CO_2$). The pH-value should then, as far as possible, be $\geq 9$. By conducting this reaction it becomes possible for the alkylamine to be reacted directly to completion. Surprisingly, in this way a reaction can be conducted at substantially higher temperatures. The result is a substantial shortening of the reaction time in comparison with DE-A-196 11 654. The reaction will already have come to an end after 15 to 20 minutes. After cooling, the N-alkyl-N'-nitroguanidine, for example the N-methyl-N'-nitroguanidine, that is formed with a high level of purity is filtered off, washed and dried. In order to prevent needles from forming during the cooling process, crystal-influencing additives, for example polyvinyl alcohol, can be added.

Alternatively, the nitroguanidine-nitrate can also be used as a starting material instead of the free nitroguanidine. The acid that is formed in this connection as a result of hydrolysis is preferably neutralized to a pH-value $\geq 9$ before the addition of alkylamine.

In addition to employing the discontinuous method, it is also possible to prepare the N-alkyl-N'-nitroguanidine, preferably the N-methyl-N'-nitroguanidine, in a continuous method. In this connection, aqueous alkylamine solution, with the alkylamines being defined as above, preferably methylamine solution is added at temperatures >60° C., is added to a stirred nitroguanidine suspension in a first reservoir. The constituents are caused to react to completion in a reservoir downstream thereof before the reaction solution is cooled in a third boiler, and the N-alkyl-N'-nitroguanidine that is formed, preferably the N-methyl-N'-nitroguanidine is filtered off. Also with this continuous method is the equilibrium shifted in the direction of the reaction end product by removing the ammonia that is formed, as described above. Both the N-alkyl-N'-nitroguanidine that is formed in the case of the discontinuous method and the N-alkyl-N'-nitroguanidine that is formed in the case of the continuous method can, if applicable, be recrystallized. The melting point of the N-methyl-N'-nitroguanidine obtained in this way in accordance with the invention amounts to 159 to 161° C.

The starting materials that are used, nitroguanidine and the alkylamines, for example the methylamine, are generally known compounds of organic chemistry. The method in accordance with the invention is, as a rule, carried out in an aqueous suspension. It is also possible, however, to operate in organic/aqueous systems, in which case all the usual organic solvents that are mixable with water can be used. Ketones, such as acetone, methyl-ethyl-ketone or methyl-isobutyl-ketone, nitriles, such as acetonitrile or proprionitrile, and also alcohols, such as methanol or ethanol, may be mentioned by way of example.

The following examples will explain the method in accordance with the invention without, however, limiting it.

EXAMPLE 1
(Discontinuous Method)

35 g nitroguanidine were suspended in 200 ml water and heated to 70° C. 40 g of 40% aqueous methylamine solution were dosed into this suspension within 5 minutes. Reaction time approximately 15 minutes. In order to remove the ammonia that had formed, air or nitrogen was blown into the reaction solution through a gassing stirrer. After cooling to approximately 5° C., the N-methyl-N'-nitroguanidine was filtered off, washed with ice water and dried. The yield amounted to 65% of the theoretical yield. The melting point of the N-methyl-N'-nitroguanidine was 162° C. The purity amounted to >98%.

EXAMPLE 2
(Discontinuous Method)

35 g nitroguanidine were suspended in 200 ml of mother liquor from Example 1, the pH-value was adjusted to approximately 9, and the reaction solution was heated to 70° C. 40 g 40% aqueous methylamine solution were dosed into this suspension within 5 minutes. Reaction time was approximately 15 minutes. In order to remove the ammonia that had formed, air or nitrogen was blown into the reaction solution through a gassing stirrer. After cooling to approximately 5° C., the N-methyl-N'-nitroguanidine was filtered off, washed with ice water and dried. The yield amounted to 85% of the theoretical yield. The melting point of the N-methyl-N'-nitroguanidine was 162° C. The purity amounted to >98%.

EXAMPLE 3

(Discontinuous Method)

35 g nitroguanidine were suspended in 200 ml water and heated to 70° C. 40 g of 40% aqueous methylamine solution were dosed into this suspension within 5 minutes. Reaction time approximately 15 minutes. During this time the pH-value was maintained between 9 and 10 by adding nitric acid. After cooling to approximately 5° C., the N-methyl-N'-nitroguanidine was filtered off, washed with ice water and dried. The yield amounted to 70% of the theoretical yield. The melting point of the N-methyl-N'-nitroguanidine was 162° C. The purity amounted to >98%.

EXAMPLE 4

(Continuous Method)

Nitroguanidine, water and 40 g methylamine solution (40%), in a ratio of 1:24:1.15, were stirred at 70° C. in the first reservoir of a cascade consisting of three stirrer vessels. The solution in the second vessel had already become clear and had reacted to completion. The solution was cooled in the third reservoir downstream thereof, to approximately 5° C. so that the N-methyl-N'-nitroguanidine precipitated. In order to remove the ammonia that had formed, air or nitrogen was blown into all the vessels. After cooling, the N-methyl-N'-nitroguanidine was filtered off, washed with ice water and dried. The yield amounted to 70% of the theoretical yield. The melting point of the N-methyl-N'-nitroguanidine amounted to 162° C. The purity amounted to >98%.

EXAMPLE 5

(Continuous Method):

Nitroguanidine nitrate was used as a starting material. Nitroguanidine nitrate, water and methylamine solution were dosed into the first vessel in a cascade consisting of four stirrer vessels, without heating. The second vessel was heated to 70° C. The pH-value was adjusted to a value of 9.5 by excess dosage of methylamine solution or by the additional addition of ammonia in the first vessel. The secondary reaction took place in the third vessel at 60 to 70° C. The fourth vessel was cooled so that the N-methyl-N'-nitroguanidine could be filtered off, washed and dried. The yield amounted to 67% of the theoretical yield. The melting point of the N-methyl-N'-nitroguanidine amounted to 160° C. The purity amounted to >98%.

What is claimed is:

1. A method for preparing N-alkyl-N'-nitroguanidine, the method comprising the step of adding metered doses of an alkylamine solution to a suspension of nitroguanadine or nitroguanidine nitrate at a temperature greater than 60° C. to form a reaction solution, whereby N-alkyl-N'-nitroguanidine is formed, and wherein ammonia that is formed in the reaction solution is removed from the reaction solution.

2. The method of claim 1 wherein the ammonia that is formed in the reaction solution is removed by passing a gas through the reaction solution.

3. The method of claim 2 wherein the gas is air, nitrogen or $CO_2$.

4. The method of claim 1 wherein the ammonia that is formed in the reaction solution is removed by adding an acid to the reaction solution, whereby the ammonia is captured by neutralization with the acid.

5. The method of claim 1 wherein at least one crystal-influencing additive is added to the reaction solution.

6. The method of claim 1 wherein the crystal-influencing additive is polyvinyl alcohol.

7. The method of claim 1 wherein the suspension of nitroguanadine or nitroguanidine nitrate includes water or organic/aqueous suspending agents.

8. The method of claim 1 wherein the suspension of nitroguanadine or nitroguanidine nitrate includes an organic/aqueous suspending agent: and wherein the organic component of the organic/aqueous suspending agent is an organic solvent that is miscible with water and that is selected from the group consisting of ketones, nitriles and alcohols.

9. The method of claim 8 wherein the organic solvent is selected from the group consisting of acetone, methyl-ethyl-ketone and methyl-isobutyl-ketone.

10. The method of claim 8 wherein the organic solvent is selected from the group consisting of acetylnitrile and proprionitrile.

11. The method of claim 8 wherein the organic solvent is selected from the group consisting of methanol and ethanol.

12. The method of claim 1 wherein the alkylamine is selected from the group consisting of benzylamine, cyclohexylamine and an alkylamine having a branched or unbranched $C_1$- to $C_6$-alkyl group.

13. The method of claim 1 wherein the alkylamine is selected from the group consisting of hexylamine, pentylamine, tert.-butylamine, butylamine, isopropylamine, propylamine, ethylamine and methylamine.

14. The method of claim 1 wherein the alkylamine is methylamine.

* * * * *